(12) United States Patent
Kagawa et al.

US006777526B2

(10) Patent No.: US 6,777,526 B2
(45) Date of Patent: Aug. 17, 2004

(54) OPTICALLY ACTIVE MALEIMIDE DERIVATIVES, OPTICALLY ACTIVE POLYMALEIMIDE DERIVATIVES, PRODUCTION METHOD THEREOF, SEPARATING AGENT USING THE SAME DERIVATIVE, AND METHOD FOR SEPARATING OPTICALLY ACTIVE COMPOUNDS USING THE SAME AGENT

(75) Inventors: Takumi Kagawa, Shinnanyo (JP); Hideo Sakka, Kudamatsu (JP)

(73) Assignee: Tosoh Corporation, Shinnanyo (JP)

( * ) Notice: Subject to any disclaimer, the term of this patent is extended or adjusted under 35 U.S.C. 154(b) by 8 days.

(21) Appl. No.: 10/226,200

(22) Filed: Aug. 23, 2002

(65) Prior Publication Data

US 2003/0069385 A1 Apr. 10, 2003

(30) Foreign Application Priority Data

Aug. 24, 2001 (JP) ........................................ 2001-254545

(51) Int. Cl.[7] .............................................. C08G 73/10
(52) U.S. Cl. ...................... 528/170; 528/310; 528/312; 528/322; 528/345; 528/392; 524/600; 524/602; 524/606; 526/258; 526/262; 210/600; 210/635; 210/656; 548/548; 502/401; 502/407; 502/439
(58) Field of Search ................................ 528/170, 310, 528/312, 322, 345, 392; 524/600, 602, 606; 526/258, 262; 210/600, 635, 656; 548/548; 502/401, 407, 439

(56) References Cited

U.S. PATENT DOCUMENTS 4,579,957 A * 4/1986 Kanayama et al. ......... 548/521

6,509,478 B2 * 1/2003 Oishi ......................... 548/549
2003/0149221 A1 * 8/2003 Oishi ......................... 528/170

FOREIGN PATENT DOCUMENTS

| EP | 1 288201 A1 | * | 3/2003 |
| JP | 60-193930 | * | 2/1985 |
| JP | 64-026523 | * | 1/1998 |
| JP | 63-41456 | * | 2/1998 |
| JP | 2003-064054 | * | 5/2003 |

OTHER PUBLICATIONS

A. La Manna, et al., Il Farmaco, Ed. Sci., vol. 20, No. 12, pp. 842–859, XP–001118795, "Optical Rotatory Dispersion Studies IV—Some Cyclohexyl– and Phenyl–Amines and Their Itaconyl–Maleyl– and Phthaloyl–Derivatives", 1965.
H. Zhou, et al., Polymer Journal, vol. 32, No. 7, pp. 552–559, XP–000958441, "Asymmetric Anionic Polymerization of of Chiral (R)–(+)–N–α–Methylbenzylmaleimide with Chiral Ligand/Organometal Complex", 2000.
Chemical Abstracts, vol. 134, No. 21, p. 1584, XP–002218943, JP 2001–106726, Apr. 17, 2001.
T. Oishi, et al., Journal of Polymer Science, vol. 38, No. 2, pp. 310–320, XP–000878169, "Asymmetric Anionic Polymerization of Maleimides Bearing Bulky Substituents", Jan. 15, 2000.
Patent Abstracts of Japan, JP 04–261145, Sep. 17, 1992.

* cited by examiner

Primary Examiner—P. Hampton Hightower
(74) Attorney, Agent, or Firm—Oblon, Spivak, McClelland, Maier & Neustadt, P.C.

(57) ABSTRACT

A separating agent that serves as an optical resolution agent is composed of a novel, useful optically active polymer. The separating agent is obtained through anionic polymerization of a novel maleimide and serves to separate optically active compounds.

13 Claims, No Drawings

OPTICALLY ACTIVE MALEIMIDE DERIVATIVES, OPTICALLY ACTIVE POLYMALEIMIDE DERIVATIVES, PRODUCTION METHOD THEREOF, SEPARATING AGENT USING THE SAME DERIVATIVE, AND METHOD FOR SEPARATING OPTICALLY ACTIVE COMPOUNDS USING THE SAME AGENT

BACKGROUND OF THE INVENTION

1. Field of the Invention

The present invention relates to novel optically active maleimide derivatives, optically active polymaleimide derivatives, production method and use thereof. Optically active polymaleimide derivatives are expected to find application as a separating agent for separating optically active compounds.

2. Description of the Prior Art

Shown below are a) optically active maleimide derivatives and b) optically active polymaleimide derivatives of the present invention:

(a) optically active maleimide derivatives. The compounds are represented by general formula (1) or (2):

(general formula (1))

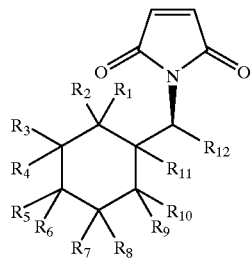

(1)

(general formula (2))

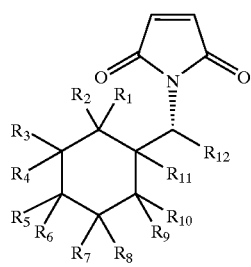

(2)

wherein $R_1$, $R_2$, $R_3$, $R_4$, $R_5$, $R_6$, $R_7$, $R_8$, $R_9$, $R_{10}$, and $R_{11}$ are each independently selected from the group consisting of hydrogen, methyl, ethyl, a straight-chained or branched alkyl having 3 to 10 carbon atoms and a straight-chained or branched alkoxy having 3 to 10 carbon atoms; and $R_{12}$ is selected from the group consisting of methyl, ethyl, n-propyl, i-propyl, n-butyl, i-butyl, tert-butyl, methoxymethyl, ethoxymethyl and ethoxyethyl.

(b) optically active polymaleimide derivatives. The polymers are represented by the following general formula (3) or (4):

(general formula (3))

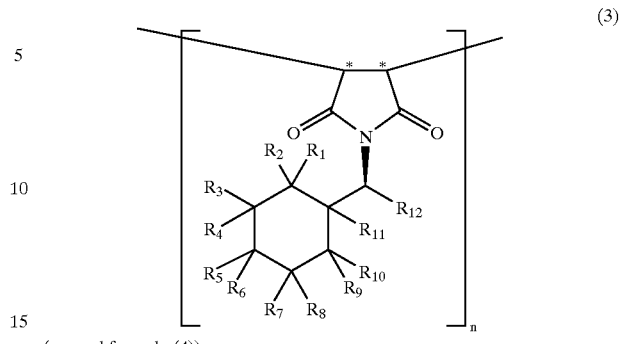

(3)

(general formula (4))

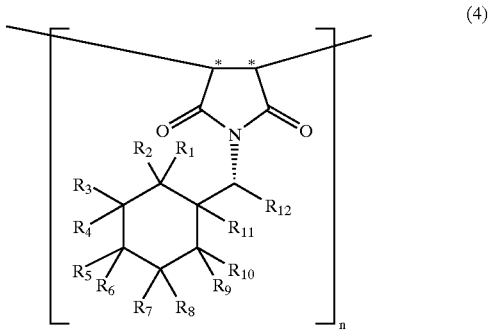

(4)

wherein $R_1$, $R_2$, $R_3$, $R_4$, $R_5$, $R_6$, $R_7$, $R_8$, $R_9$, $R_{10}$, and $R_{11}$, are each independently selected from the group consisting of hydrogen, methyl, ethyl, a straight-chained or branched alkyl having 3 to 10 carbon atoms and a straight-chained or branched alkoxy having 3 to 10 carbon atoms; $R_{12}$ is selected from the group consisting of methyl, ethyl, n-propyl, i-propyl, n-butyl, i-butyl, tert-butyl, methoxymethyl, ethoxymethyl and ethoxyethyl; n is an integer from 2 to 10000; and an asterisk represents an asymmetric carbon.

None of these compounds has been known to date, nor has any proposal been made to use these compounds as a separating agent for separating optical isomers.

Many optically active synthetic polymers that can be used as optical resolution agents are known, including optically active poly(triphenylmethyl methacrylate) disclosed in Japanese Patent Laid-Open Publication No. Sho 56-106907, optically active polyacrylamide disclosed in Japanese Patent Laid-Open Publication No. Sho 56-167708, and polyacrylamide disclosed in Japanese Patent Laid-Open Publication No. Sho 63-14446, which has a side chain including an optically active substituent and chemically bound to silica gel surfaces.

Despite the relatively high resolution that these optically active polymers can achieve when applied to separate certain types of optically active compounds, the polymers can be applied only to a limited range of racemic mixtures. For this reason, a need exists for novel polymers that have a wide range of applicability and specific performance.

Further, advancement in technologies and instruments for analysis has given rise to a demand for separating agents with a higher resolution.

SUMMARY OF THE INVENTION

In an effort to develop a novel separating agent capable of separating optical isomers at high resolution, the present inventors have discovered novel optically active maleimide derivatives as shown by the general formulae (1) and (2)

above and novel optically active polymaleimide derivatives as shown by the general formulae (3) and (4) above that can be prepared by allowing the optically active maleimide derivatives to undergo asymmetric anionic polymerization, and found that these polymaleimide derivatives can serve as highly effective separating agents for separating optical isomers.

Accordingly, the present invention provides optically active maleimide derivatives of the general formulae (1) and (2), optically active polymaleimide derivatives of the general formulae (3) and (4), production methods of optically active polymaleimide derivatives of the general formulae (3) and (4), and use of optically active polymaleimide derivatives of the general formulae (3) and (4).

DETAILED DESCRIPTION OF THE PREFERRED EMBODIMENT

The present invention will now be described in detail.

Optically active maleimide derivatives of the present invention as represented by the general formula (1) or (2) can be obtained by reacting respective optically active 1-cyclohexyl-1-aminoethane derivatives with maleic anhydride. Specifically, the optically active maleimide derivatives of the present invention of the general formula (1) or (2) can be obtained by reacting maleic anhydride with optically active 1-cyclohexyl-1-aminoethane derivatives represented by the following general formula (7) or (8):

(general formula (7))

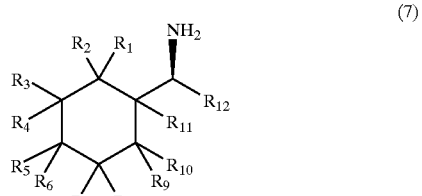

(7)

(general formula (8))

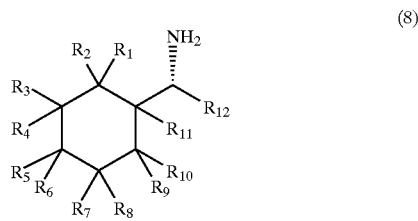

(8)

wherein the substituents $R_1$ through $R_{12}$ are identical to those defined above. While the optically active maleimide derivatives of the present invention may be produced by any method, it is produced for example by mixing an optically active 1-cyclohexyl-1-aminoethane derivative with an equimolar amount of maleic anhydride in an inactive solvent such as toluene and adding a dehydration agent such as hexamethyldisilazane to carry out reaction.

Examples of the optical active maleimide derivative of the present invention as represented by the general formula (1) or (2) include (S)-(−)-1-cyclohexylethyl-1-maleimide, (S)-(−)-1-(2-methylcyclohexyl)ethyl-1-maleimide, (S)-(−)-1-(2,6-dimethylcyclohexyl)ethyl-1-maleimide, (S)-(−)-1-(3,5-dimethylcyclohexyl)ethyl-1-maleimide, (S)-(−)-1-(2-ethylcyclohexyl)ethyl-1-maleimide, (S)-(−)-1-(2,6-diethylcyclohexyl)ethyl-1-maleimide, (S)-(−)-1-(3,5-diethylcyclohexyl)ethyl-1-maleimide, (S)-(−)-1-(2-i-propylcyclohexyl)ethyl-1-maleimide, (S)-(−)-1-(2,6-di-i-propylclohexyl)ethyl-1-maleimide, (S)-(−)-1-(3,5-di-i-propylclohexyl)ethyl-1-maleimide, (S)-(−)-1-(2-n-butylcyclohexyl)-ethyl1-maleimide, (S)-(−)-1-(2,6-di-n-butylcyclohexy)ethyl-1-maleimide, (S)-(−)-1-(3,5-di-n-butylcyclohexyl)ethyl-1-maleimide, (S)-(−)-1-(2-t-butylcyclohexyl)ethyl-1-maleimide, (S)-(−)-1-(2,6-di-t-butylcyclohexyl)ethyl-1-maleimide, (S)-(−)-1-(3,5-di-t-butylcyclohexyl)ethyl-1-maleimide, (S)-(−)-1-(2-methylcyclohexyl)propyl-1-maleimide, (S)-(−)-1-(2,6-dimethylcyclohexyl)propyl-1-maleimide, (S)-(−)-1-(3,5-dimethylcyclohexyl)propyl-1-maleimide, (S)-(−)-1-(2-ethylcyclohexyl)propyl-1-maleimide, (S)-(−)-1-(2,6-diethylcyclohexyl)propyl-1-maleimide, (S)-(−)-1-(3,5-diethylcyclohexyl)propyl-1-maleimide, (S)-(−)-1-(2-i-propylcyclohexyl)propyl-1-maleimide, (S)-(−)-1-(2,6-di-i-propylcyclohexyl)propyl-1-maleimide, (S)-(−)-1-(3,5-di-i-propylcyclohexyl)propyl-1-maleimide, (S)-(−)-1-(2-n-butylcyclohexyl)propyl-1-maleimide, (S)-(−)-1-(2,6-di-n-butylcyclohexyl)propyl-1-maleimide, (S)-(−)-1-(3,5-di-n-butylcyclohexyl)propyl-1-maleimide, (S)-(−)-1-(2-t-butylcyclohexyl)propyl-1-maleimide, (S)-(−)-1-(2,6-di-t-butylcyclohexyl)propyl-1-maleimide, (S)-(−)-1-(3,5-di-t-butylcyclohexyl)propyl-1-maleimide, (S)-(−)-1-(2-methoxycyclohexyl)ethyl-1-maleimide, (S)-(−)-1-(2,6-di-methoxycyclohexyl)ethyl-1-maleimide, (S)-(−)-1-(3,5-di-methoxycyclohexyl)ethyl-1-maleimide, (S)-(−)-1-(2-t-butoxymethoxycyclohexyl)ethyl-1-maleimide, (S)-(−)-1-(2,6-di-t-butoxycyclohexyl)ethyl-1-maleimide, and (S)-(−)-1-(3,5-di-t-butoxycyclohexyl)ethyl-1-maleimide. (R)-forms of the compound, which have configurations identical to mirror images of the respective (S)-forms, are also included.

The optically active polymaleimide derivatives of the general formula (3) or (4) can be prepared by allowing the optically active maleimide derivatives of the general formula (1) or (2) to undergo asymmetric anionic polymerization.

While the asymmetric anionic polymerization in the present invention may be carried out in any manner, it can be carried out for example by dissolving an asymmetric ligand in a reaction solvent along with an anionic polymerization catalyst, then adding to the solvent an optically active maleimide derivative to serve as the material, and allowing the reaction to proceed.

Examples of the anionic polymerization catalyst for use in the present invention include organometallic catalysts such as n-butyllithium, fluorenyllithium, diethyl zinc, and dimethyl zinc. The catalysts are typically used in an amount of 0.1 to 30 mol % with respect to the amount of the optically active maleimide derivative to serve as the material for the reaction.

Examples of the optically active ligand for use in the anionic polymerization process in the present invention include (−)-sparteine (hereinafter abbreviated as Sp) represented by the following formula (6):

(formula (6))

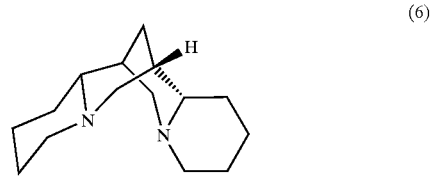

(6)

and a bisoxazoline derivative represneted by the following formula (5):

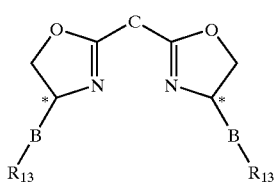

(5)

wherein the substituents indicated by $R_{13}$ are each independently selected from the group consisting of methyl, ethyl, a straight-chained, branched or cyclic, aliphatic hydrocarbon, either saturated or unsaturated, having 3 to 8 carbon atoms, and a substituted or unsubstituted aromatic hydrocarbon having 6 to 20 carbon atoms, the substituents of the substituted aromatic hydrocarbon each independently selected from the group consisting of methyl, ethyl, a straight-chained, branched or cyclic aliphatic hydrocarbon, either saturated or unsaturated, having 3 to 8 carbon atoms, and an aromatic hydrocarbon having 6 to 20 carbon atoms; B represents methylene chain having 0 to 5 carbon atoms; C represents alkylidene or an aromatic group having 1 to 10 carbon atoms; and an asterisk represents an optically active carbon.

Examples of the bisoxazoline derivative for use in the present invention include (4S)-2,2'-(1-ethylpropylidene)bis[4-(1-phenylethyl)-4,5-dihydrooxazole], (4S)-2,2'-(1-ethylpropylidene)bis[4-(1-(1-naphthyl)ethyl)-4,5-dihydrooxazole], (4S)-2,2'(1-methylethylidene)bis [4-(1-phenylethyl)-4,5-dihydrooxazole], (4S)-2,2'-(cyclopropylidene)bis[4-(1-phenylethyl)-4,5-dihydrooxazole], (4S)-2,2'-(1,3-phenyl)bis[4-(1-phenylethyl)-4,5-dihydrooxazole], and (4S)-2,2'-(2,6-pyridyl)bis[4-(1-phenylethyl)-4,5-dihydrooxazole]. While in theory, the bisoxazoline derivative may be used in an equimolar amount of the anionic polymerization catalyst used in the reaction, it is preferably used in an amount of 1.02 to 1.5 moles per one mole of the material to ensure stable reaction.

Examples of the solvent suitable for use in the asymmetric anionic polymerization of the present invention may be any solvent that shows substantially no reactivity to the reaction and include, but are not limited to, ether solvents, such as diethylether, di-n-propylether, di-i-propylether, di-n-butylether, di-t-butylether and tetrahydrofuran (abbreviated as THF, hereinafter), and aromatic hydrocarbon solvents, such as benzene, toluene, xylene, ethylbenzene, and mesitylene.

While the solvent may be used in any amount in the asymmetric anionic polymerization of the present invention, it is typically used in an amount by weight that is twice to 100 times the amount of the optically active maleimide derivative used in the reaction.

While the reaction temperature to carry out the asymmetric anionic polymerization in the present invention may vary depending on the conditions for the reaction, it is typically in the range of −78° C. to 100° C.

While the reaction time to carry out the asymmetric anionic polymerization in the present invention may vary depending on the type of the catalyst and the reaction temperature, it is typically in the range of 1 hour to 240 hours to bring the reaction to completion.

Once the reaction is completed, the reaction solution is added dropwise to a solvent, such as hexane, heptane, methanol, ethanol and isopropanol, that little dissolves the reaction product, so that the optically active polymaleimide derivative of the present invention crystallizes out and thus can be collected in the form of powder. The collected product may further be dissolved in a solvent, such as THF and toluene, and then be recrystallized out in methanol or other solvents to increase the purity.

The optically active polymaleimide derivatives of the present invention as represented by the general formula (3) or (4) find a wide range of applications when used as a separating agent for separating optically active substances.

The optically active polymaleimide derivative for use as the separating agent of the present invention may be any polymer that is obtained through polymerization of the optically active maleimide derivative of the general formula (1) or (2) and specifically includes poly[(S)-1-cyclohexylethyl-1-maleimide], poly[(S)-1-(2-methylcyclohexyl)ethyl-1-maleimide], poly[(S)-1-(2,6-dimethylcyclohexyl)ethyl-1-maleimide], poly[(S)-1-(3,5-dimethylcyclohexyl)ethyl-1-maleimide], poly[(S)-1-(2-ethylcyclohexyl)ethyl-1-maleimide], poly[(S)-1-(2,6-diethylcyclohexyl)ethyl-1-maleimide], poly[(S)-1-(3,5-diethylcyclohexyl)ethyl-1-maleimide], poly[(S)-1-(2-i-propylcyclohexyl)ethyl-1-maleimide], poly[(S)-1-(2,6-di-i-propylcyclohexyl)ethyl-1-maleimide], poly[(S)-1-(3,5-di-i-propylcyclohexyl)ethyl-1-maleimide], poly[(S)-1-(2-n-butylcyclohexyl)ethyl-1-maleimide], poly[(S)-1-(2,6-di-n-butylcyclohexyl)ethyl-1-maleimide], poly[(S)-1-(3,5-di-n-butylcyclohexyl)ethyl-1-maleimide], poly[(S)-1-(2-t-butylcyclohexy)ethyl-1-maleimide], poly[(S)-1-(2,6-di-t-butylcyclohexyl)ethyl-1-maleimide], poly[(S)-1-(3,5-di-t-butylcyclohexyl)ethyl-1-maleimide], poly[(S)-1-(2-methylcyclohexyl)propyl-1-maleimide], poly[(S)-1-(2,6-dimethylcyclohexyl)propyl-1-maleimide], poly[(S)-1-(3,5-dimethylcyclohexyl)propyl-1-maleimide], poly[(S)-1-(2-ethylcyclohexyl)propyl-1-maleimide], poly[(S)-1-(2,6-diethylcyclohexyl)propyl-1-maleimide], poly[(S)-1-(3,5-diethylcyclohexyl)propyl-1-maleimide], poly[(S)-1-(2-i-propylcyclohexyl)propyl-1-maleimide], poly[(S)-1-(2,6-di-i-propylcyclohexyl)propyl-1-maleimide], poly[(S)-1-(3,5-di-i-propylcyclohexyl)propyl-1-maleimide], poly[(S)-1-(2-n-butylcyclohexyl)propyl-1-maleimide], poly[(S)-1-(2,6-di-n-butylcyclohexyl)propyl-1-maleimide], poly[(S)-1-(3,5-di-n-butylcyclohexyl)propyl-1-maleimide], poly[(S)-1-(2-t-butylcyclohexyl)propyl-1-maleimide], poly[(S)-1-(2,6-di-t-butylcyclohexyl)propyl-1-maleimide], poly[(S)-1-(3,5-di-t-butylcyclohexyl)propyl-1-maleimide], poly[(S)-1-(2-methoxycyclohexyl)ethyl-1-maleimide], poly[(S)-1-(2,6-dimethoxycyclohexyl)ethyl-1-maleimide], poly[(S)-1-(3,5-dimethoxycyclohexyl)ethyl-1-maleimide], poly[(S)-1-(2-t-butoxymethoxycyclohexyl)ethyl-1-maleimide], poly[(S)-1-(2,6-di-t-butoxycyclohexyl)ethyl-1-maleimide], and poly[(S)-1-(3,5-di-t-butoxycyclohexyl)ethyl-1-maleimide]. Also included are polymers obtained when (R)-form monomers, which have configurations identical to mirror images of the respective (S)-forms, have undergone the asymmetric anion polymerization.

The separating agent of the invention comprising the optically active polymaleimide derivative of the general formula (3) or (4) finds a wide range of applications for separating optically active substances.

The separating agent of the present invention encompasses not only the optically active polymaleimide derivatives of the general formula (3) or (4) but also carriers carrying the optically active polymaleimide derivatives of the general formula (3) or (4).

Examples of the carrier for use in the separating agent of the present invention includes silica gel, alumina, cross-linked polystyrene, polyacrylate derivatives, polysiloxane and those obtained by treating surfaces of these carriers with alkylsilane. Preferably, the carrier has the particle size of 1 μm to 200 μm and the average pore size of 10 to 3000 angstroms for use in high speed liquid chromatography (HPLC) or gas chromatography analysis.

The carrier may carry the optically active polymaleimide derivatives of the present invention in any manner. For example, a porous carrier can physically carry the optically active polymaleimide derivative through physical contact, or functional groups may be attached to polymer terminals of the optically active polymaleimide derivative so that the porous carrier can chemically bind to the polymer.

While the amount of the optically active polymaleimide derivative of the present invention carried by the carrier is not limited to a specific range and may vary depending on the type and physical properties of the carrier, it is typically in the range of 1 to 50 wt % with respect to the weight of the carrier.

The separating agent obtained by having the optically active polymaleimide derivative of the present invention carried by the porous carrier can be widely used for separating optically active compounds. For example, when used as a filler to be packed in HPLC columns, the separating agent shows wide applicability both in normal phases that use eluant system such as hexane-isopropanol and in reverse phases that use eluant system such as alcohol-water. Furthermore, the optically active polymaleimide derivative of the present invention finds application not only as a filler for HPLC columns, but also as a shift reagent used in nuclear magnetic resonance spectroscopy (abbreviated as NMR, hereinafter) spectroscopy as well as a carrier for optical resolution columns used in gas chromatography.

The manner of the present invention in which the separating agent comprising the optically active polymaleimide derivative optically active is used to separate optically active substances is not limited to a particular manner. For example, it is used in HPLC and gas chromatography to facilitate the separation of optically active substances. It may also be used as a shift reagent in NMR.

As set forth, the present invention provides optically active novel maleimide derivatives as well as optically active polymaleimide derivatives. The separating agent made from the optically active polymaleimide derivative of the present invention is of significant usefulness when used as a separating agent for separating optical isomers.

EXAMPLES

While the present invention will now be described in further detail, the description is by way of example only and is not intended to limit the scope of the invention in any way.

The average molecular weight of each of optically active polymaleimide derivatives was determined relative to polystyrene standard by gel permeation chromatography (high performance GPC system manufactured by TOSOH Co., Ltd.) and optical rotation was determined using SEPA-300 manufactured by HORIBA Co., Ltd. The mass spectrum of each polymaleimide derivative was determined using M-80B manufactured by HITACHI Co., Ltd., and $^1$H-NMR and $^{13}$C-NMR were performed on Gemini 200 manufactured by VARIAN Co., Ltd. IR spectrum was obtained using 2000 FT-IR manufactured by PERKIN ELMER Co., Ltd.

The resolution of each of the optically active polymaleimide derivatives prepared was determined using a multipump CCPM, a UV-Visible light detector UV-8020, and an integrator Chromatocorder 21, each manufactured by TOSOH Co., Ltd.

Example 1

Preparation of (S)-(−)-N-1-cyclohexylethyl-1-maleimide

In a 500 ml round-bottomed, three-necked flask equipped with a cooling condenser, a drop funnel and a stirrer, 2.94 g (30.0 mmol) of maleic anhydride and 155 ml of dry benzene were placed and were stirred to dissolve the solute. The mixture was then cooled to 0° C. on an ice bath.

To the mixture, 3.82 g (30.0 mmol) of (S)-(+)-1-cyclohexyl-1-aminoethane in 65 ml of dry benzene was added dropwise using the drop funnel. The mixture was allowed to warm to room temperature and then was stirred for 1 hour.

4.09 g (30.0 mmol) of zinc chloride was added to the reaction mixture while the mixture was vigorously stirred. The mixture was then heated to 80° C. on an oil bath, followed by dropwise addition of 9.68 g (60.0 mmol) hexamethyldisilazane in 78 ml of dry benzene with the drop funnel. Subsequently, the mixture was refluxed for 5 hours, while heated, to allow the reaction to proceed.

Once the reaction was completed, the mixture was allowed to cool to room temperature, washed with 0.5N hydrochloric acid, extracted with ethyl acetate, washed with a saturated solution of sodium hydrogen carbonate, washed with a saturated solution of sodium chloride, dried on anhydrous magnesium sulfate, and condensed to obtain crude (S)-(−)-N-1-cyclohexylethyl-1-maleimide. The resultant (S)-(−)-N-1-cyclohexylethyl-1-maleimide was further purified by a column chromatography (n-hexane/ethyl acetate=4/1, vol/vol) followed by distillation (88° C./0.1 mmHg) to obtain 5.5 g of a colorless oil product (89% yield).

Specific rotation: $[\alpha]_D^{25}$=−6.5° (C=1.0, THF, 1=10 cm). $^1$H-NMR (CDCl$_3$): δ 6.64 (s, 2H), 4.00–3.72 (m, 1H), 1.38 (d, 3H, J=7.2 Hz), 2.05–0.75 (m, 11H). $^{13}$C-NMR (CDCl$_3$): δ 170.73, 133.54, 52.04, 39.99, 30.36, 29.94, 26.02, 25.71, 25.60, 16.17. MASS (m/z): 208 ([M+H]$^+$). IR (KBr; vcm$^{-1}$): 3090, 2930, 2851, 1702, 1450, 1405, 1242, 1196, 1176, 1124, 839, 693. Element analysis: C 69.2, H 14.0, N 6.7 (Calc.; C 69.5, H 14.1, N 6.7).

Example 2

In a 50 ml eggplant-shaped flask with a magnetic stirrer placed therein, 100 (0.83 mmol) of diethyl zinc, 230 mg (1.00 mmol) of (−)-sparteine and 17.5 ml of toluene were placed and were stirred for 30 minutes at −11° C. To the resulting mixture, 2.07 g of (S)-(−)-N-1-cyclohexylethyl-1-maleimide (10.00 mmol) obtained in Example 1 was added and the mixture was maintained at the same temperature for the subsequent 96 hours to allow the reaction to proceed.

After the reaction was completed, the reaction mixture was poured into 200 ml methanol and the mixture was filtered. The resulting filtrate was then dried at room temperature under a reduced pressure to obtain 1.12 g of optically active poly(N-1-cyclohexylethyl-1-maleimide), a desired product, which was a reddish viscous product (63% yield).

Number-average molecular weight (Mn)=16.7×103, Mw/Mn=10.2. Specific rotation $[\alpha]_{435}^{25}$=378.1° (C=0.1, CHCl$_3$). $^1$H-NMR (CDCl$_3$): δ 4.10–3.40 (b, 1H), 2.30–0.40 (b, 16H). $^{13}$C-NMR (CDCl$_3$): δ 176.89, 53.76, 42.96, 38.88, 30.29, 25.75, 15.80, 15.34. IR (KBr; vcm$^{-1}$): 2931, 2854, 1695, 1450, 1400, 1372, 1247, 1202, 1126, 748, 652. Element analysis: C 69.1, H 14.3, N 6.6 (Calc.; C 69.5, H 14.1, N 6.7).

Example 3

Preparation of Silica Gel Carrying 10% Optically Active poly(N-1-cyclohexylethyl-1-maleimide) (Specific Rotation $[\alpha]_{435}^{25}$=378.1°) (C=0.1, CHCl$_3$) and a Column Packed with the Silica Gel In a 50 ml eggplant-shaped flask, 500 mg of optically active poly(N-1-cyclohexylethyl-1-maleimide) (Specific rotation $[\alpha]_{435}^{25}=378.1°$) (C=0.1, CHCl$_3$) was placed along with 10 ml chloroform to dissolve the polymer in chloroform. To this solution, 4.5 g of silica gel (average particle size=10 μm, average pore size=100 angstrom) was added and chloroform was subsequently removed by a vacuum rotary evaporator to obtain 5 g of silica gel carrying 10% optically active poly(N-1-cyclohexylethyl-1-maleimide) (Specific rotation $[\alpha]_{435}^{25}=378.1°$)(C=0.1, CHCl$_3$) as desired product.

The resultant silica gel carrying 10% optically active poly(N-1-cyclohexylethyl-1-maleimide)(Specific rotation $[\alpha]_{435}^{25}=378.1°$) (C=0.1, CHCl$_3$) was dispersed in methanol and then was injected with a high-pressure pump into a 4.6 mmID×150 mmL stainless steel column at a flow rate of 3.5 ml/min with maximum pressure of 400 kg/cm$^2$ to fill the column. The number of theoretical plates was determined to be 2276 plates.

The number of theoretical plates was determined by using methanol as an eluant and toluene as a solute and was calculated according to the following equation.

The number of theoretical plates (N)=5.54×[Tr/W1/2]$^2$, where Tr=retention time (sec), W1/2=width of the peak measured at one-half the peak height.

Examples 4 through 7

The column prepared in Example 3 was used to separate different compounds under the conditions shown in Table 1 below. The results are also shown in Table 1.

TABLE 1

| Examples | Compound[1] | Mobile phase[2] | Flow rate ml/min | K1'[3] | K2'[4] | α[5] |
|---|---|---|---|---|---|---|
| 4 | A | (1) | 1.0 | 1.66 | 1.78 | 1.07 |
| 5 | B | (1) | 1.0 | 0.71 | 2.77 | 3.91 |
| 6 | C | (1) | 1.0 | 0.27 | 0.81 | 3.03 |
| 7 | D | (1) | 1.0 | 0.61 | 2.45 | 4.01 |

[1]Compound A: (±)-2,3-dihydro-2-(benzyloxymethyl)-4H-pyran-4-one
Compound B: trans-2,3-epoxy-1,3-diphenylpropane-1-one
Compound C: trans-1,2-epoxy-1-(2-fluorophenyl)-4,4-dimethylpentane-3-one
Compound D: trans-2,3-epoxy-1-phenyl-3-(2-chlorophenyl)propane-1-one
[2]mobile phase (1): n-hexane/isopropanol = 90/10 (vol/vol)
[3]k1': retention coefficient of enantiomer that is eluted first.
k1' = (t1 − t0)/t0
(value obtained for 1,3,5-tri-tert-butylbenzene was used as t0)
[4]k2': retention coefficient of enantiomer that is eluted second.
k2' = (t2 − t0)/t0
(value obtained for 1,3,5-tri-tert-butylbenzene was used as t0)
[5]α: separation coefficient
α = k2'/k1'

What is claimed is:

1. An optically active maleimide derivative represented by general formula (1) or (2):

(general formula (1))

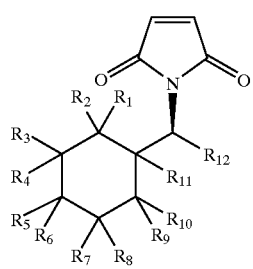

(1)

-continued (general formula (2))

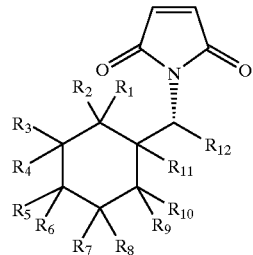

(2)

wherein R$_1$, R$_2$, R$_3$, R$_4$, R$_5$, R$_6$, R$_7$, R$_8$, R$_9$, R$_{10}$, and R$_{11}$ are each independently selected from the group consisting of hydrogen, methyl, ethyl, a straight-chained or branched alkyl having 3 to 10 carbon atoms and a straight-chained or branched alkoxy having 3 to 10 carbon atoms; and R$_{12}$ is selected from the group consisting of methyl, ethyl, n-propyl, i-propyl, n-butyl, i-butyl, tert-butyl, methoxymethyl, ethoxymethyl and ethoxyethyl, wherein the optically active maleimide derivative is not an optically active N-1-cyclohexvlethyl-1-maleimide, wherein each of the substituents R$_1$ through R$_{11}$ is hydrogen and R$_{12}$ is methyl in the general formula (1) or (2).

2. An optically active polymaleimide derivative represented by the following general formula (3) or (4):

(general formula (3))

(3)

(general formula (4))

(4)

wherein R$_1$, R$_2$, R$_3$, R$_4$, R$_5$, R$_6$, R$_7$, R$_8$, R$_9$, R$_{10}$, and R$_{11}$ are each independently selected from the group consisting of hydrogen, methyl, ethyl, a straight-chained or branched alkyl having 3 to 10 carbon atoms and a straight-chained or branched alkoxy having 3 to 10 carbon atoms; R$_{12}$ is selected from the group consisting of methyl, ethyl, n-propyl, i-propyl, n-butyl, i-butyl, tert-butyl, methoxymethyl, ethoxymethyl and ethoxyethyl; n is an integer from 2 to 10000; and an asterisk represents a asymmetric carbon.

3. A method for producing the optically active polymaleimide derivative of claim 2, comprising the step of allowing an optically active maleimide derivative to undergo asymmetric anionic polymerization, wherein the optically active maleimide derivative is represented by general formula (1) or (2):

(general formula (1))

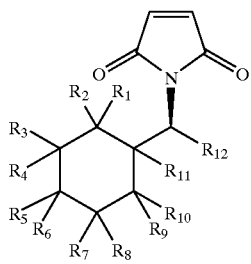

(1)

(general formula (2))

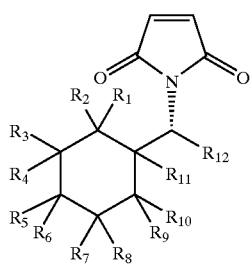

(2)

4. The method according to claim 3, wherein the asymmetric anionic polymerization is carried out in the presence of an asymmetric ligand represented by the following general formula (5):

(general formula (5))

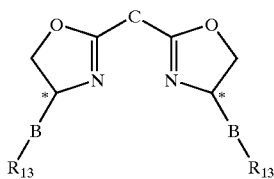

(5)

wherein the substituents indicated by $R_{13}$ are each independently selected from the group consisting of methyl, ethyl, a straight-chained, branched or cyclic aliphatic hydrocarbon, either saturated or unsaturated, having 3 to 8 carbon atoms, and a substituted or unsubstituted aromatic hydrocarbon having 6 to 20 carbon atoms, the substituents of the substituted aromatic hydrocarbon each independently selected from the group consisting of methyl, ethyl, a straight-chained, branched or cyclic aliphatic hydrocarbon, either saturated or unsaturated, having 3 to 8 carbon atoms and an aromatic hydrocarbon having 6 to 20 carbon atoms; B represents methylene having 0 to 5 carbon atoms; C represents alkylidene or an aromatic group having 1 to 10 carbon atoms; and an asterisk represents an optically active carbon, or represented by the following formula (6):

(formula (6))

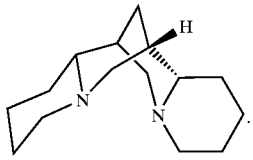

(6)

5. A separating agent comprising the optically active polymaleimide derivative of claim 2.

6. A separating agent comprising a carrier carrying the optically active polymaleimide derivative of claim 2.

7. A method for separating optically active compounds, wherein the separating agent of claim 5 is used.

8. A method for separating optically active compounds, wherein the separating agent of claim 6 is used.

9. A method for separating optically active compounds, wherein high speed liquid chromatography is performed using a column packed with the separating agent of claim 5 to separate optically active compounds.

10. A method for separating optically active compounds, wherein high speed liquid chromatography is performed using a column packed with the separating agent of claim 6 to separate optically active compounds.

11. A method for producing the optically active maleimide derivative of claim 1 represented by the general formula (1) or (2), the method comprising the step of reacting maleic anhydride with an optically active 1-cyclohexyl-1-aminoethane derivative represented by the following general formula (7) or (8):

(general formula (7))

(7)

(general formula (8))

(8)

wherein $R_1$, $R_2$, $R_3$, $R_4$, $R_5$, $R_6$, $R_7$, $R_8$, $R_9$, $R_{10}$, and $R_{11}$ are each independently selected from the group consisting of hydrogen, methyl, ethyl, a straight-chained or branched alkyl having 3 to 10 carbon atoms and a straight-chained or branched alkoxy having 3 to 10 carbon atoms; and $R_{12}$ is selected from the group consisting of methyl, ethyl, n-propyl, i-propyl, n-butyl, i-butyl, tert-butyl, methoxymethyl, ethoxymethyl and ethoxyethyl.

12. An optically active poly(N-1-cyclohexylethyl-1-maleimide), wherein each of the substituents $R_1$ through $R_{11}$ is hydrogen and $R_{12}$ is methyl in the general formula (3) or (4) in claim 2.

13. A method for producing the optically active poly(N-1-cyclohexylethyl-1-maleimide) of claim 12, comprising the step of allowing an optically active N-1-cyclohexylethyl-1-maleimide to undergo asymmetric anionic polymerization.

* * * * *